US012139699B2

(12) United States Patent
Hirayama et al.

(10) Patent No.: US 12,139,699 B2
(45) Date of Patent: Nov. 12, 2024

(54) MAGNETIC-FIELD GENERATOR FOR A CELL SHEET

(71) Applicants: DHF America, LLC, Raleigh, NC (US); National University Corporation Tokai National Higher Education and Research System, Aichi-ken (JP)

(72) Inventors: Kotaro Hirayama, Tokyo (JP); Hotaka Kayano, Tokyo (JP); Shota Tanoue, Tokyo (JP); Yuki Watanabe, Tokyo (JP); Toshio Kokuryo, Aichi-ken (JP); Rei Shibata, Aichi-ken (JP); Akira Ito, Aichi-ken (JP); Toyoaki Murohara, Aichi-ken (JP)

(73) Assignees: DHF AMERICA, LLC, Raleigh, NC (US); NATIONAL UNIVERSITY CORPORATION TOKAI NATIONAL HIGHER EDUCATION AND RESEARCH SYSTEM, Aichi-Ken (JP)

( * ) Notice: Subject to any disclaimer, the term of this patent is extended or adjusted under 35 U.S.C. 154(b) by 108 days.

(21) Appl. No.: 17/995,892

(22) PCT Filed: Apr. 13, 2021

(86) PCT No.: PCT/US2021/027083
§ 371 (c)(1),
(2) Date: Oct. 10, 2022

(87) PCT Pub. No.: WO2021/211584
PCT Pub. Date: Oct. 21, 2021

(65) Prior Publication Data
US 2023/0126629 A1    Apr. 27, 2023

Related U.S. Application Data

(60) Provisional application No. 63/011,001, filed on Apr. 16, 2020.

(51) Int. Cl.
*B03C 1/03*    (2006.01)
*B03C 1/033*   (2006.01)
(Continued)

(52) U.S. Cl.
CPC .......... *C12M 35/06* (2013.01); *B03C 1/0335* (2013.01); *B03C 1/288* (2013.01); *B03C 1/30* (2013.01);
(Continued)

(58) Field of Classification Search
CPC ...... C12M 35/06; C12M 25/02; C12M 33/04; C12M 41/12; C12M 47/02; C12M 47/04;
(Continued)

(56) References Cited

U.S. PATENT DOCUMENTS

| 4,110,222 A | 8/1978 | Watson |
| 5,523,231 A | 6/1996 | Reeve |

(Continued)

FOREIGN PATENT DOCUMENTS

| CN | 202465700 U | * 10/2012 | ............ C12M 47/04 |
| CN | 202533709 U | * 11/2012 | ............... H01F 3/00 |
| WO | 2019/155035 A1 | 8/2019 | |

OTHER PUBLICATIONS

English translation of Patent Publication CN 202533709U, published Nov. 14, 2012. (Year: 2012).*

(Continued)

*Primary Examiner* — Joseph W Drodge
(74) *Attorney, Agent, or Firm* — Greer, Burns & Crain, Ltd

(57) ABSTRACT

A magnetic-field generator (10) is provided to be used in construction of a cell sheet (12), and include s a magnetic circuit assembly (24) configured to generate a magnetic field for the construction of the cell sheet (12) using magnetic force caused by the magnetic field wherein the magnetic (Continued)

force is substantially transverse to a plane defined by the cell sheet (12), and a power control system (44) configured to generate and control electric power to magnetically charge the magnetic circuit assembly (24) using the electric power.

17 Claims, 6 Drawing Sheets

(51) Int. Cl.
    *B03C 1/28*     (2006.01)
    *B03C 1/30*     (2006.01)
    *C12M 1/12*     (2006.01)
    *C12M 1/26*     (2006.01)
    *C12M 1/34*     (2006.01)
    *C12M 1/42*     (2006.01)

(52) U.S. Cl.
    CPC ............ *C12M 25/02* (2013.01); *C12M 33/04* (2013.01); *C12M 41/12* (2013.01); *B03C 2201/18* (2013.01)

(58) Field of Classification Search
    CPC ...... C12M 47/06; B03C 1/0335; B03C 1/288; B03C 1/30; B03C 2201/18; B03C 2201/26; B03C 1/031; B03C 1/033; B03C 1/04; B03C 1/08; B03C 2201/22; B01D 21/009; B01D 35/06; H01F 3/00; H01F 3/10; H01F 3/14
    See application file for complete search history.

(56) References Cited

U.S. PATENT DOCUMENTS

| | | | |
|---|---|---|---|
| 2002/0109571 A1* | 8/2002 | Fujiwara | ................... H01F 3/10 336/178 |
| 2011/0286975 A1 | 11/2011 | Souza et al. | |
| 2012/0295302 A1 | 11/2012 | Lamish et al. | |
| 2015/0070124 A1* | 3/2015 | Kapoor | ..................... H01F 3/08 336/211 |
| 2016/0108392 A1* | 4/2016 | Stelling | .............. C12N 15/1013 506/40 |

OTHER PUBLICATIONS

English translation of Patent Publication CN 202465700U, published Oct. 3, 2012. (Year: 2012).*

International Search Report and Written Opinion received for PCT/US2021/027083, mailed Jul. 21, 2021.

International Preliminary Report on Patentablity received for PCT/US2021/027083, dated Mar. 15, 2022.

* cited by examiner

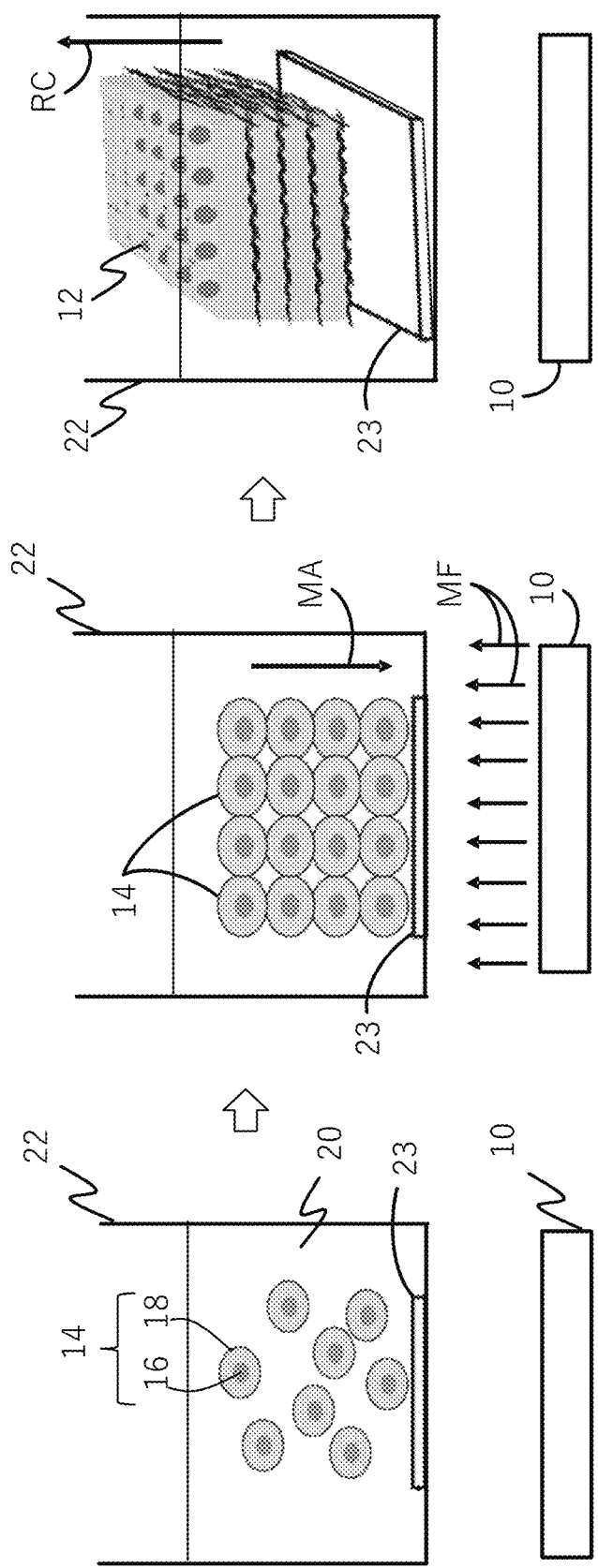

MAGNETIC-FIELD GENERATOR FOR A CELL SHEET

RELATED APPLICATION

This application claims priority under 35 USC 119 from U.S. Provisional Application No. 63/011,001 filed Apr. 16, 2020, the contents of which are incorporated by reference herein.

BACKGROUND

The present invention relates to a system of constructing a cell sheet, and more specifically relates to a magnetic-field generator utilized for constructing the cell sheet under the action of magnetic force.

Various cell sheet construction systems, such as temperature-responsive, electro-responsive, photo-responsive, pH-responsive, mechanical, or magnetic systems, are utilized for constructing the cell sheet (e.g., a mesenchymal stem cell sheet). Existing magnetic systems use magnetite cationic liposomes (MCLs) having a positive surface charge for achieving improved adsorption by cells.

For example, multilayered sheets of magnetically-labeled (e.g., MCL-labeled) cells can be formed in an ultralow-attachment plate using a magnetic system. Thus, the multilayered cell sheet having the cells labeled with MCLs is constructed under the action of magnetic force. Such magnetic systems also control cell sheet shape, thickness, and/or configuration.

For a clinical application, each cell sheet needs a sufficient strength and thickness to allow effective transplantation. Constructing the cell sheet having a practically sufficient strength to achieve a high therapeutic effect is a difficult task. Using the magnetic system, a cell layer mixed with a gel including collagen and basement membrane components with the magnetically-labeled cells can be constructed by attracting the cells using the magnetic force.

However, one disadvantage of the existing magnetic system is that the magnetic force associated with a magnetic field generated by the magnetic system is not evenly applied to the magnetically-labeled cells due to variable magnetic field strengths generated by one or more magnets of the magnetic system. Multiple magnets can be used to generate a sufficient magnetic force to construct a larger cell sheet having a predetermined thickness.

Yet, depending on an overall size of the cell sheet, not all regions of the cell sheet are covered by the magnets, thereby unevenly leaving certain regions of the cell sheet without sufficient magnetic force. Such uneven magnetic force of the magnets typically causes a weak region in the cell sheet, and thus the cell sheet becomes prone to rupture and/or slippage during use.

Another disadvantage of the existing magnetic system is that it is difficult to control an amount of the magnetic force of the magnets once installed in the magnetic system. As such, it is difficult to construct a different thickness of the cell sheet which can be used to treat a different clinical injury. Although the magnets of the magnetic system can be replaceable, such changes in the magnetic system during clinical operation can be time-consuming, cost-inhibitive, and thus impractical.

Thus, there is a need to develop an enhanced magnetic system for construction of the cell sheet that overcomes one or more above-described disadvantages of the existing magnetic systems.

SUMMARY

In one embodiment of the present disclosure, a magnetic-field generator is provided to be used in construction of a cell sheet. The magnetic-field generator includes a magnetic circuit assembly configured to generate a magnetic field for the construction of the cell sheet using magnetic force caused by the magnetic field wherein the magnetic force is substantially transverse to a plane defined by the cell sheet, and a power control system configured to generate and control electric power to magnetically charge the magnetic circuit assembly using the electric power.

In one example, the magnetic circuit assembly includes at least one core member and at least one table member, and a width of the at least one table member is greater than a width of the at least one core member. In a variation, the at least one core member has an outer region and an inner region, and a magnetic permeability of the outer region is different from the magnetic permeability of the inner region. In one variation, the magnetic permeability of the outer region is lower than the magnetic permeability of the inner region. In another variation, the at least one core member has at least one slit disposed at an outer surface of the at least one core member.

In another example, the power control system is configured to adjust a power level of the electric power.

In yet another example, the magnetic-field generator further includes a cooling system configured to cool the magnetic circuit assembly.

In still another example, the magnetic-field generator further includes an extraction device configured to extract a culture supernatant associated with the cell sheet.

In still yet another example, the magnetic circuit assembly is made of a ferromagnetic material having low magnetic coercivity.

In a further example, the magnetic-field generator further includes a power manager configured to diminish unwanted residual magnetism associated with the magnetic circuit assembly.

In yet a further example, the magnetic force being substantially transverse penetrates the cell sheet and a direction of the penetrating magnetic force is approximately ninety degrees with respect to the plane defined by the cell sheet.

In still a further example, the at least one table member includes a first table member and a second table member. In a variation, the first table member and the second table member are distantly disposed such that an air gap is created between the first table member and the second table member. In another variation, the air gap is configured for facilitating insertion of a culture vessel having the cell sheet.

In still yet a further example, the magnetic-field generator further includes a passageway disposed in the at least one core member and the at least one table member in fluid communication with one another, and configured to facilitate extraction of at least a portion of the cell sheet.

The methods, systems, and apparatuses disclosed herein may be implemented in any means for achieving various aspects. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which:

FIGS. 1A, 1B, and 1C illustrate schematic diagrams of an exemplary process performed for the construction of the cell sheet using the magnetic-field generator of FIG. 1;

Figure 1:
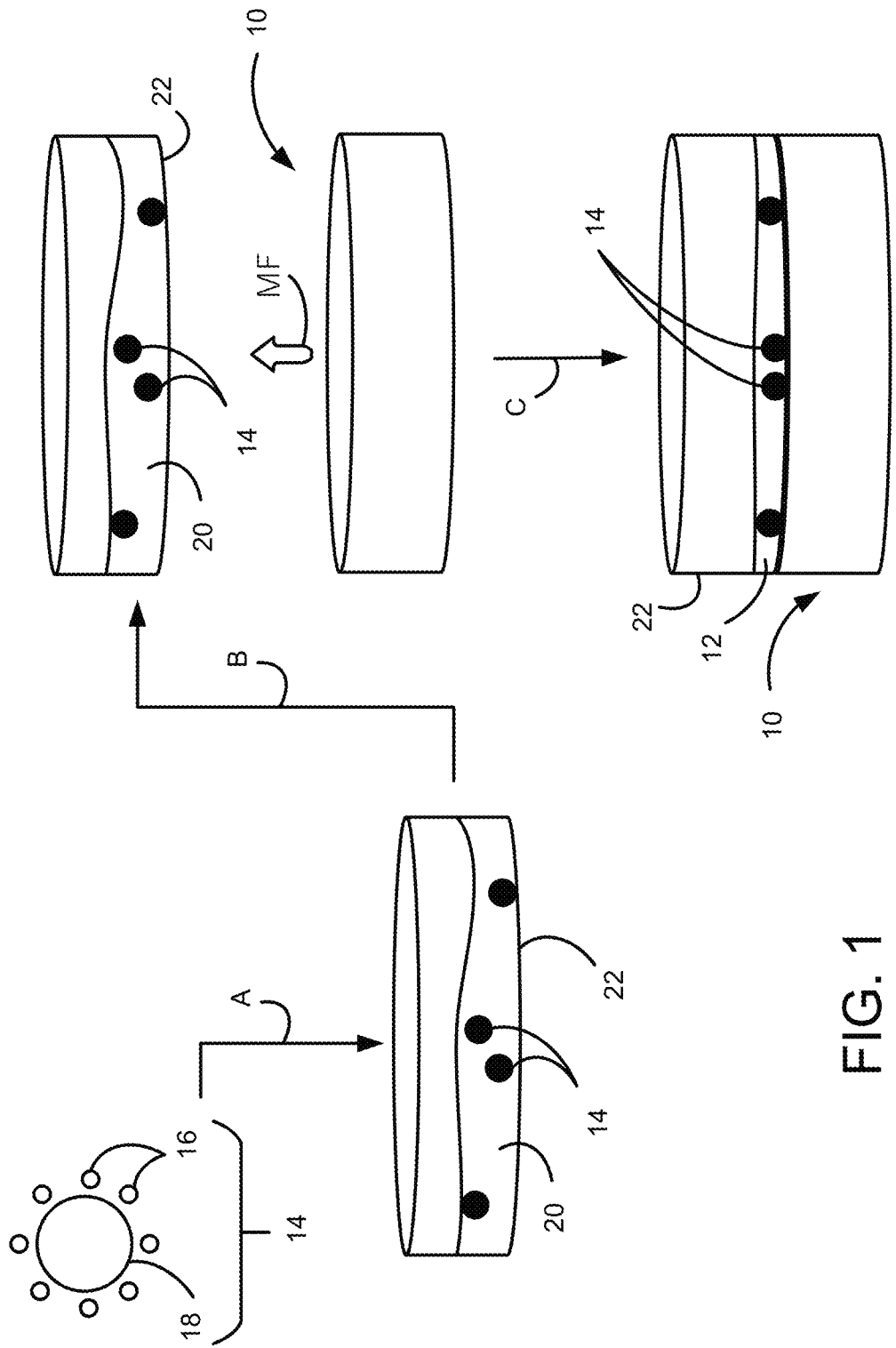
FIG. 1 illustrates a schematic diagram of an exemplary magnetic-field generator used in construction of a cell sheet in accordance with embodiments of the present disclosure.

Other features of the present embodiments will be apparent from the accompanying drawings and from the detailed description that follows.

DETAILED DESCRIPTION

Embodiments of the present disclosure will be described in detail herebelow with reference to the attached drawings.

Referring now to FIGS. 1 and 1A-1C, an exemplary magnetic-field generator 10 used in construction of a cell sheet 12 is shown in accordance with embodiments of the present disclosure. In the illustrated embodiment, the magnetic-field generator 10 is configured to generate and substantially evenly distribute a magnetic field for constructing the cell sheet 12 by consistently attracting magnetically-labeled cells 14 having magnetic particles 16.

In one embodiment, the cell sheet 12 is derived from induced pluripotent stem cells (iPS cells) 18. Exemplary magnetically-labeled cells 14 include fetal liver kinase-1 positive (Flk-1$^+$) cells induced from the iPS cells, which are also referred to as vascular progenitor cells (VPCs). Thus, in one embodiment, the cell sheet 12 is constructed using the iPS cell-derived Flk-1$^+$ cells.

A term "magnetically-labeled" cell refers to a cell having a magnetization capability enabling an introduction or adhesion of magnetic particles 16 to stem cells 18, thereby allowing the operation of the magnetically-labeled cells 14 by magnetic force. In one embodiment, the magnetic particles 16 are particles held by each stem cell 18, and can magnetize the stem cell 18 holding the magnetic particles 16.

For example, the magnetic particles 16 can be particles of a magnetic material, such as iron oxide including ferrite and magnetite, chromic oxide, and cobalt. Two or more different types of magnetic particles 16 can also be combined to suit the application.

In one embodiment, the magnetic particles 16 are encapsulated in lipid membrane, such as liposome. For example, a magnetite liposome prepared by encapsulating the magnetic particles 16 in the liposome, or the MCL can be used. In one embodiment, the MCL is taken into the stem cells 18 by hydrophobic interaction or electrical interaction with a cell surface.

Such an intake of the magnetic particles 16 allows reliable magnetic labeling of the stem cells 18. In embodiments, multiple magnetic particles 16 are held by each stem cell 18, such that the magnetically-labeled cells 14 can be readily manipulated by the magnetic force generated by the magnetic-field generator 10. As sequentially illustrated by arrows A, B, and C, the magnetically-labeled cells 14 can be magnetically pulled together to form the cell sheet 12 using a magnetic field MF created by the magnetic-field generator 10.

As shown in FIG. 1A, for example, the magnetically-labeled cells 14 are mixed with a gel or liquid material 20 and placed in a culture vessel 22 for facilitating formation of a cell layer. For example, the gel material 20 can include type I collagen, laminin composing the basement membrane, type IV collagen, and/or entactin. In one embodiment, an attachment layer 23 is used to readily remove the cell sheet 12 having the magnetically-labeled cells 14 from the culture vessel 22.

As shown in FIG. 1B, for example, the magnetic-field generator 10 applies magnetic force caused by the magnetic field, as illustrated by arrows MF, while the culture vessel 22 is placed. By magnetic attraction, as illustrated by an arrow MA, of the magnetically-labeled cells 14 incorporating the MCL, the magnetically-labeled cells 14 can be cultivated three-dimensionally for a predetermined time period.

In one embodiment, the magnetic-field generator 10 has a substantially "C"-shaped or substantially "E"-shaped configuration, as described in greater detail below, it is not particularly limited to these shapes. For example, any suitable shapes, such as oval, square, or irregular three-dimensional configurations, are contemplated to suit different applications. In some embodiments, the magnetic force of the magnetic-field generator 10 can be applied from all surrounding directions, e.g., including up, down, and sides of the culture vessel 22.

As shown in FIGS. 1B and 1C, for example, in the illustrated embodiment, the magnetic force caused by the magnetic field MF of the magnetic-field generator 10 is applied to the bottom surface of the culture vessel 22 for a predetermined time period for drawing the magnetically-labeled cells 14 near the bottom surface of the culture vessel 22. Subsequently, the gel material 20 is gelated and incubated with the culture vessel 22 at a predetermined temperature, e.g., approximately 37 degrees Celsius (° C.) for a predetermined time period.

A sheet-like structure formed by such gelation becomes the cell sheet 12. In one embodiment, as illustrated by an arrow RC, the cell sheet 12 is cultivated on the attachment layer 23, such as an ultra-low attachment surface, and subsequently can be recovered by peeling the cell sheet 12 from the bottom surface of the culture vessel 22 when the magnetic force is released.

Figure 2:
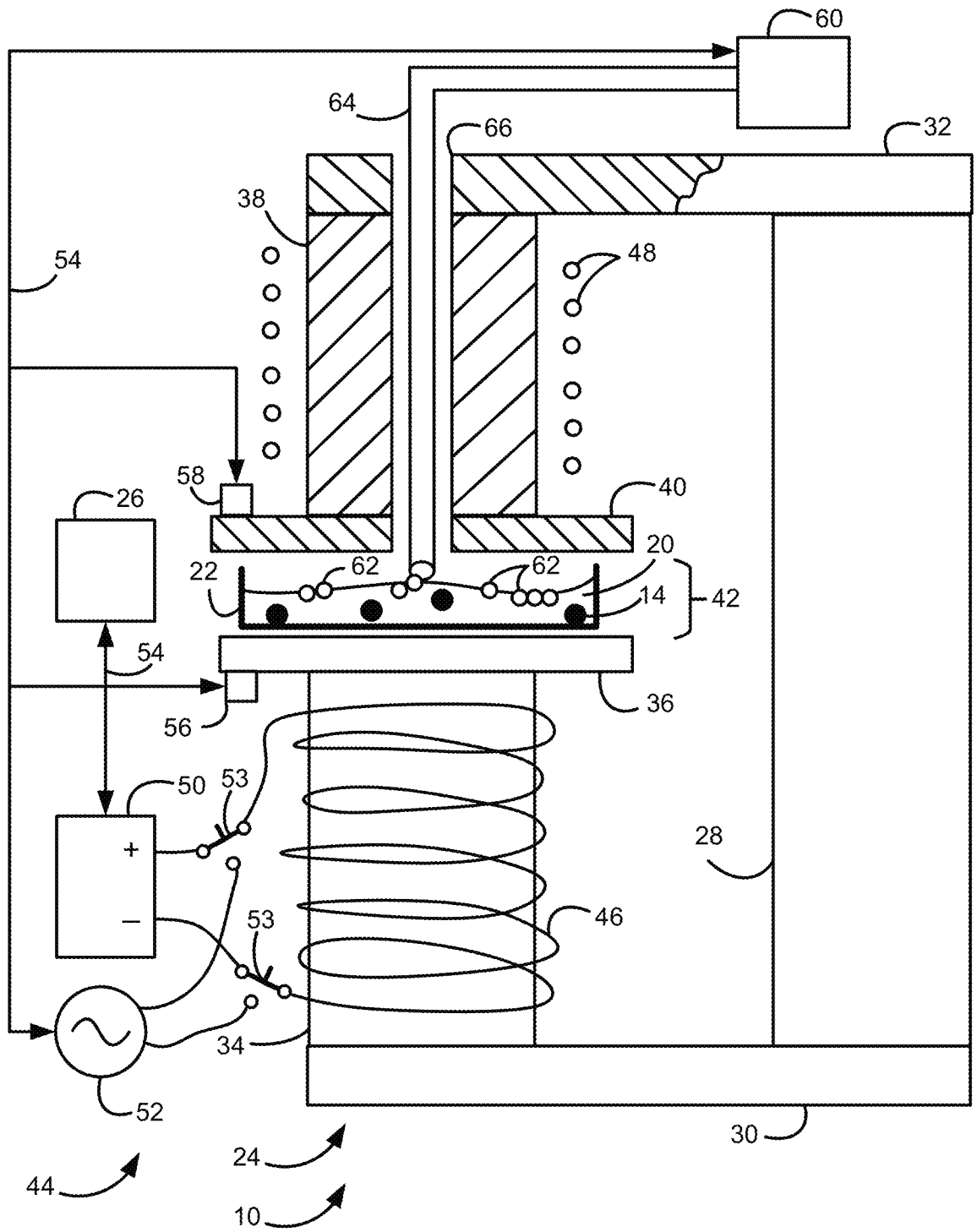
FIG. 2 illustrates a schematic diagram of the magnetic-field generator of FIG. 1, featuring a magnetic circuit assembly.

Referring now to FIG. 2, an exemplary configuration of the magnetic-field generator 10 is shown in accordance with embodiments of the present disclosure. In the illustrated embodiment, the magnetic-field generator 10 includes a magnetic circuit assembly 24 configured to generate the magnetic field for constructing the cell sheet 12 (FIG. 1), and a controller 26 configured to control an overall operation of the magnetic-field generator 10.

Included in the magnetic circuit assembly 24 is a support member 28 connected at one end to a first arm member 30, and at an opposite end to a second arm member 32. In one embodiment, the magnetic circuit assembly 24 further includes a first core member 34 that is connected at one end to the first arm member 30 and at an opposite end to a first table member 36. Similarly, the magnetic circuit assembly 24 further includes a second core member 38 that is connected at one end to the second arm member 32 and at an opposite end to a second table member 40.

In some embodiments, the magnetic circuit assembly 24 includes the support member 28, the first arm member 30, the second arm member 32, the first core member 34, the first table member 36, the second core member 38, and the second table member 40. In the illustrated embodiment, above components 28, 30, 32, 34, 36, 38, and 40 of the magnetic circuit assembly 24 have a generally "C"-shaped configuration, and are shown as separate independent mechanisms. In other embodiments, the components of the magnetic circuit assembly 24 can be integrated as a single unit to suit different applications.

Figure 2A:
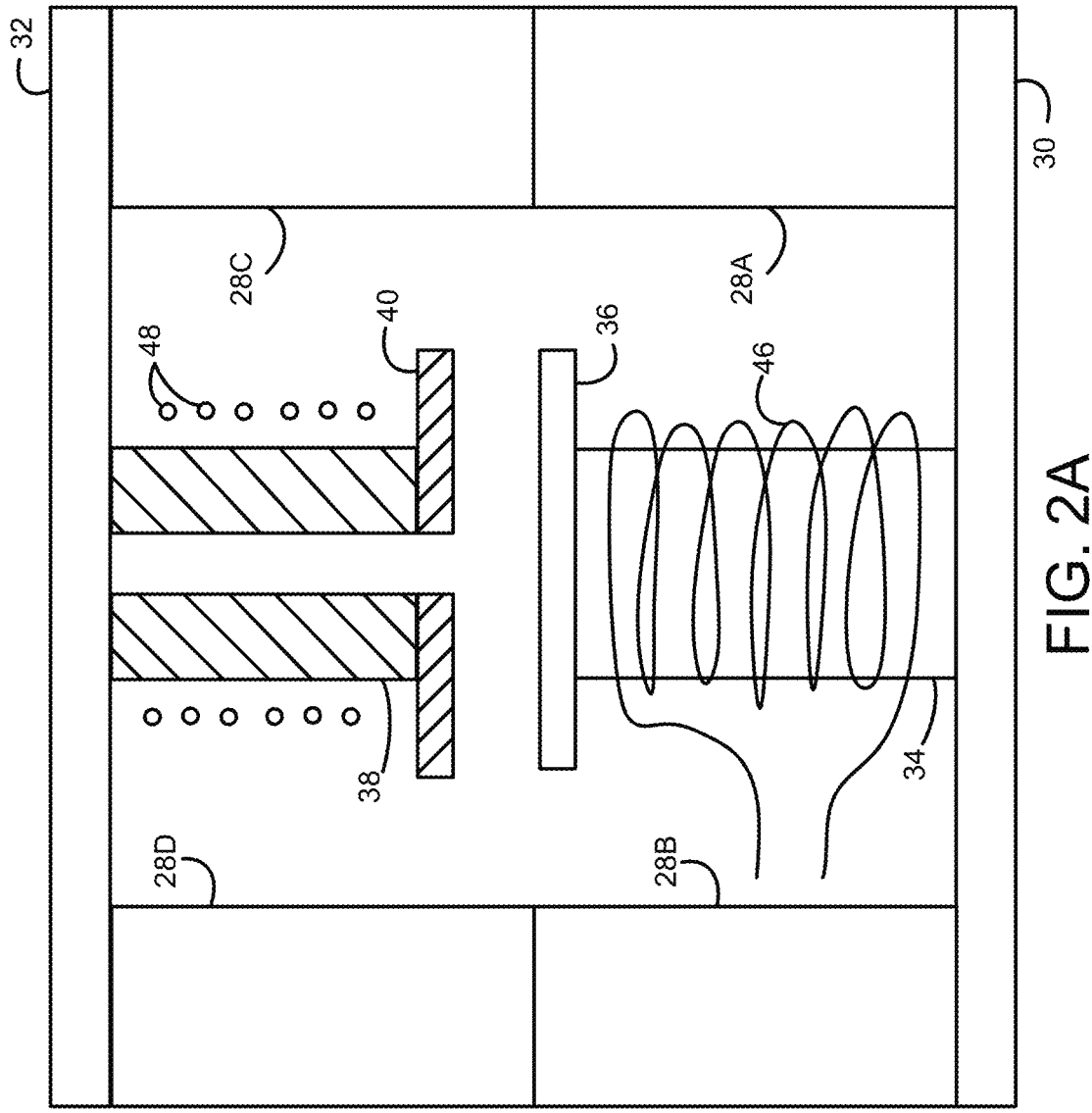
FIG. 2A illustrates a schematic diagram of the magnetic-field generator of FIG. 1, featuring another magnetic circuit assembly.

Referring now to FIG. 2A, in another embodiment, the components, 28, 30, 32, 34, 36, 38, and 40 of the magnetic circuit assembly 24 have a generally "E"-shaped configuration to suit different applications. In the illustrated embodiment, the first arm member 30 is extended such that the first arm member 30 is magnetically connected at one end to a first support member 28A, and at an opposite end magnetically connected to a second support member 28B. In FIG. 2A, the first arm member 30, the first support member 28A, the second support member 28B, and the first core member 34 disposed between the first support member 28A and the second support member 28B have the "E"-shaped configuration.

Similarly, in the illustrated embodiment, the second arm member 32 is extended such that the second arm member 32 is magnetically connected at one end to a third support member 28C, and at an opposite end magnetically connected to a fourth support member 28D. In FIG. 2A, the second arm member 32, the third support member 28C, the fourth support member 28D, and the second core member 38 disposed between the third support member 28C and the fourth support member 28D have the "E"-shaped configuration.

Returning now to FIG. 2, in one embodiment, the first table member 36 and the second table member 40 are separately or distantly disposed such that an air gap 42 is created between the first table member 36 and the second table member 40. In use, the air gap 42 provides space for facilitating insertion of the culture vessel 22 having the magnetically-labeled cells 14. For example, the culture vessel 22 is initially placed on a top surface of the first table member 36 in the air gap 42 before generating the magnetic force.

In one embodiment, when the culture vessel 22 is inserted into the air gap 42, the culture vessel 22 is slidably disposed or fitted within the air gap 42 such that the top surface of the first table member 36 is in direct contact with the culture vessel 22. Similarly, when the culture vessel 22 is inserted into the air gap 42, the culture vessel 22 is slidably disposed or fitted within the air gap 42 such that a lower surface of the second table member 40 is in direct contact with the culture vessel 22. In certain embodiments, there are no gaps between the first table member 36 and the culture vessel 22, and between the second table member 40 and the culture vessel 22.

In another embodiment, when the culture vessel 22 is inserted into the air gap 42, the culture vessel 22 is slidably disposed or fitted within the air gap 42 such that the lower surface of the second table member 40 is spaced from the culture vessel 22 at a predetermined distance. In one example, an exemplary distance between the lower surface of the second table member 40 and the culture vessel 22 is approximately one (1) millimeter. However, other suitable distances (e.g., less than 1 millimeter but greater than zero millimeter) are also contemplated to suit different applications.

To facilitate generation of the magnetic field, the components 28, 30, 32, 34, 36, 38, and 40 of the magnetic circuit assembly 24 are magnetically connected to one another and made of ferromagnetic metal, such as iron, carbon steel, and the like, or ferromagnetic compounds, such as ferrites. During operation, the magnetic force and magnetomotive force induced by an electric current are magnetically transmitted via the magnetic circuit assembly 24 to generate the magnetic field between the first table member 36 and the second table member 40.

A power control system 44 configured to generate and control electric power is included in the magnetic-field generator 10. In one embodiment, the power control system 44 includes a first coil 46 associated with the first core member 34, and a second coil 48 associated with the second core member 38. Using the first coil 46 and the second coil 48, the power control system 44 magnetically charges the magnetic circuit assembly 24.

In one embodiment, the first coil 46 and the second coil 48 are not connected, and are configured separately and independently with separate power sources. For example, each of the first coil 46 and the second coil 48 is connected to a different first power supply respectively, and is configured such that power is supplied from the respective power supply.

The connection method of the first coil 46 and the second coil 48 can use various connection methods to suit the application. In another embodiment, the first coil 46 and the second coil 48 are connected in series, and the power can be supplied from one common power source. In yet another embodiment, the first coil 46 and the second coil 48 can be connected in parallel, and the power can be supplied from the one common power source.

In one embodiment, each coil 46, 48 is capable of carrying an electric current received from a power source, such as a direct current (DC) power source 50 that produces a direct current voltage, or an alternating current (AC) power source 52. A switch 53 can be used to select between the DC power source 50 and the AC power source 52. In one embodiment, the first coil 46 is wound on an outer surface of the first core member 34, and similarly the second coil 48 is wound on an outer surface of the second core member 38.

To generate the magnetic force, the controller 26 of the power control system 44 instructs the power source 50 or 52 to supply the electric power to the first coil 46 and the second coil 48. When the electric power is supplied to the first coil 46 and the second coil 48, the magnetic field is generated surrounding the first core member 34 and the second core member 38 for magnetically attracting the magnetically-labeled cells 14 in the culture vessel 22. In one embodiment, an exemplary power level of the electric power ranges between approximately 50 and 500 watts (50~500 W).

In the illustrated embodiment, the controller 26 is communicably connected to the power control system 44 via a communication link 54. In one embodiment, the controller 26 includes computer readable program instructions stored in one of memories of electronic controllers in the controller 26 and executed by a respective processor of the electronic controllers, or other computer usable medium. In another embodiment, the controller 26 includes a module or controller, which may or may not be independent from one of the electronic controllers of the magnetic-field generator 10.

In one embodiment, the magnetic-field generator 10 includes a temperature sensor 56 communicably connected to the controller 26 of the power control system 44 via the communication link 54. In one embodiment, the temperature sensor 56 is configured to measure a current temperature of the magnetic-field generator 10, such as the first table member 36.

Figure 7:
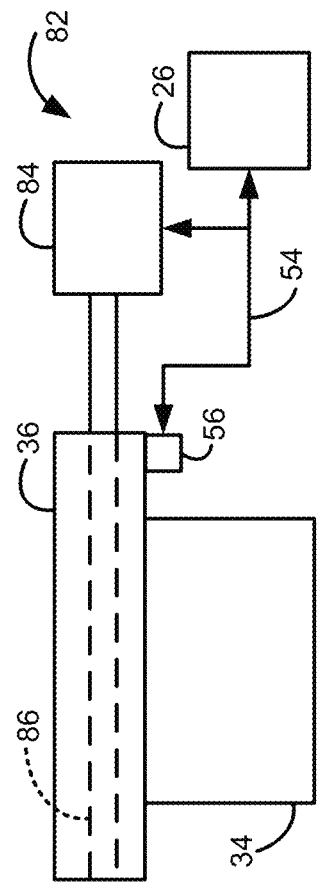
FIG. 7 illustrates a schematic diagram of a cooling system used with the magnetic circuit assembly of FIG. 2.

For example, during operation, the controller 26 receives information about the current temperature of the first table member 36 from the temperature sensor 56, and controls a temperature control unit, such as a cooling system 82 shown in FIG. 7, based on the current temperature of the first table member 36. In some embodiments, one or more temperature sensors 56 can be disposed at any suitable locations of the magnetic-field generator 10, such as the second table member 40 and/or the first core member 34.

In another embodiment, the magnetic-field generator 10 includes an optional magnetic flux sensor 58 communicably connected to the controller 26 of the power control system 44 via the communication link 54. In one embodiment, the magnetic flux sensor 58 is configured to measure a magnetic inductance or magnetic field strength of the magnetic-field generator 10, such as the second table member 40. In some embodiments, one or more magnetic flux sensor 58 can be disposed at any suitable locations of the magnetic-field generator 10, such as the first table member 36 and/or the first core member 34.

In yet other embodiments, a separate or independent magnetic flux meter (not shown) can be used to measure the magnetic inductance or magnetic field strength of the magnetic-field generator 10. For example, during operation, the controller 26 receives information about the magnetic inductance or magnetic field strength of the second table member 40 from the magnetic flux sensor 58, and selectively adjust or change the power level supplied to the second coil 48.

In one embodiment, the magnetic-field generator 10 includes an extraction device 60 communicably connected to the controller 26 of the power control system 44 via the communication link 54. In one embodiment, the extraction device 60 is configured to extract a culture supernatant 62 in the gel material 20. In the illustrated embodiment, the extraction device 60, such as a vacuum pump, is connected to a conduit 64 configured to receive the culture supernatant 62.

In the illustrated embodiment, a passageway 66, such as an aperture or a channel, is disposed in the second arm member 32, the second core member 38, and the second table member 40 in fluid communication with one another. In one embodiment, the passageway 66 is configured to facilitate insertion of the conduit 64 for extracting the culture supernatant 62. For example, during operation, the controller 26 instructs the extraction device 60 to extract the culture supernatant 62 through the conduit 64 for a predetermined time period.

In one embodiment, the passageway 66 is configured to facilitate extraction of at least one of: the culture supernatant 62, the gel material 20, and the magnetically-labeled cells 14 in the culture vessel 22. In one example, the conduit 64 is inserted at least partially into the passageway 66 such that a lower end of the conduit 64 is capable of extracting the culture supernatant 62, for example, using a suction force.

An exemplary inner diameter of the passageway 66 is approximately three (3) millimeters. However, other suitable diameters (e.g., less than 3 millimeters) are also contemplated to suit different applications.

Figure 3:
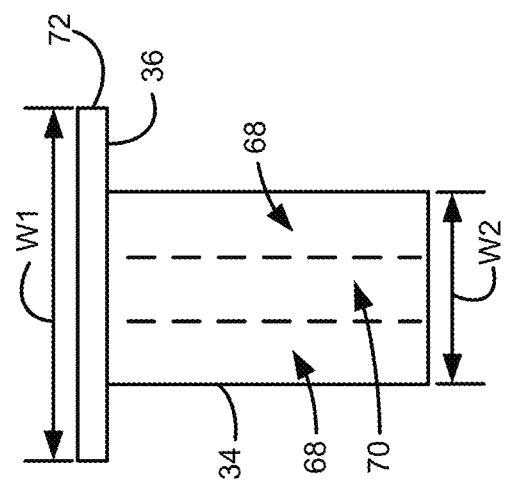
FIG. 3 is a side view of a first embodiment of the magnetic circuit assembly of FIG. 2.

Referring now to FIG. 3, a first embodiment of the first core member 34 and the first table member 36 of the magnetic-field generator 10 is shown in accordance with embodiments of the present disclosure. When the first core member 34 and the first table member 36 are magnetically charged by the power control system 44 (FIG. 2), a magnetic flux density of a radially outer region 68 of the first core member 34 is typically greater than the magnetic flux density of an inner region 70 of the first core member 34.

Thus, to evenly distribute the magnetic field around the first table member 36, a table width (or diameter) designated W1 of the first table member 36 is greater than a core width (or diameter) designated W2 of the first core member 34. In one embodiment, the table width W1 is at least thirty percent (30%) longer than the core width W2.

In this configuration, the magnetic field transmitted from the outer region 68 of the first core member 34 is dispersed along an outer periphery 72 of the first table member 36. Consequently, the magnetic force associated with the magnetic field is substantially evenly applied to the magnetically-labeled cells 14 in the culture vessel 22 (FIG. 2), thereby attracting and spreading the magnetically-labeled cells 14 substantially evenly toward the top surface of the first table member 36. As such, the magnetic force applied substantially transversely to a plane (e.g., a layer) defined by the cell sheet 12 is also substantially evenly distributed. Consequently, the magnetically-labeled cells 14 in the culture vessel 22 are substantially evenly spread near an inner bottom surface of the culture vessel 22.

In another embodiment, when the magnetic-field generator 10 is operated without the first table member 36, the magnetically-labeled cells 14 in the culture vessel 22 are evenly spread near the top surface of the first core member 34. Such magnetic force causes generation of a stronger cell sheet due to even distribution of the magnetically-labeled cells 14 in the cell sheet 12.

In one embodiment, the magnetic force applied substantially transversely refers to the magnetic force penetrating the cell sheet 12 cross-sectionally and having a direction of the penetrating magnetic force being approximately ninety degrees (90°) with respect to the plane defined by the cell sheet 12. For example, the magnetic circuit assembly 24 generates the magnetic field that causes and initiates the magnetic force such that the magnetic force penetrates the cell sheet 12 at approximately 90° with respect to the plane defined by the cell sheet 12.

Figure 4:
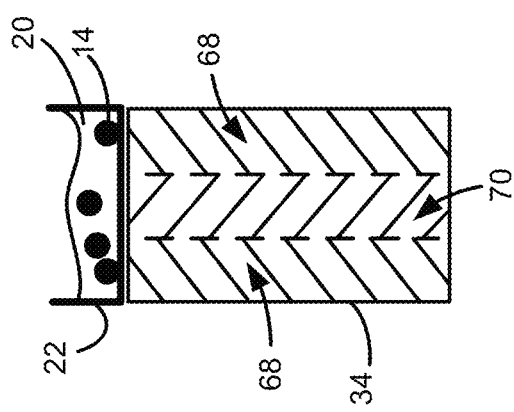
FIG. 4 is a vertical cross-sectional view of a second embodiment of the magnetic circuit assembly of FIG. 2.

Referring now to FIG. 4, a second embodiment of the first core member 34 of the magnetic-field generator 10 is shown in accordance with embodiments of the present disclosure. In the illustrated embodiment, the magnetic-field generator 10 is operated without the first table member 36. For example, the culture vessel 22 having the magnetically-labeled cells 14 can be placed directly on a top surface of the first core member 34.

As discussed, the magnetic flux density of the radially outer region 68 of the first core member 34 is typically greater than the magnetic flux density of the inner region 70 of the first core member 34. However, the first core member 34 can be made in a specific manner that a magnetic permeability of the first core member 34 is variable with respect to different regions of the first core member 34.

In one embodiment, to evenly distribute the magnetic field around the top surface of the first core member 34, the outer region 68 of the first core member 34 is made of the ferromagnetic metal having the magnetic permeability that is lower than the magnetic permeability of the inner region 70. Thus, the first core member 34 can be made of two or more materials having different magnetic permeabilities.

In the illustrated embodiment, because the magnetic permeability of the outer region 68 is lower than the magnetic permeability of the inner region 70, a formation of the magnetic flux is resisted more in the outer region 68 of the first core member 34 than in the inner region 70 of the first core member 34. Also, the magnetic flux in transmission around the inner region 70 of the first core member 34 is less resisted than around the outer region 68 of the first core member 34.

Thus, the magnetic force associated with the magnetic flux density is substantially equal near the top surface of the first core member 34 due to the different magnetic permeabilities in the first core member 34. As a result, the magnetic force is substantially evenly applied to the magnetically-labeled cells 14 in the culture vessel 22. As such, the magnetic force applied substantially transversely to a plane (e.g., a layer) defined by the cell sheet 12 is also substantially evenly distributed.

Figure 5:
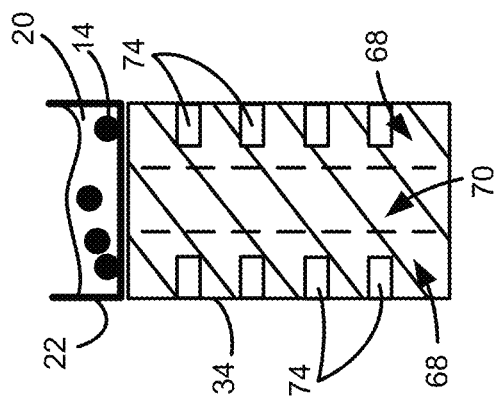
FIG. 5 is a vertical cross-sectional view of a third embodiment of the magnetic circuit assembly of FIG. 2.

Referring now to FIG. 5, a third embodiment of the first core member 34 of the magnetic-field generator 10 is shown in accordance with embodiments of the present disclosure. In the illustrated embodiment, the magnetic-field generator 10 is operated without the first table member 36. For example, the culture vessel 22 having the magnetically-labeled cells 14 can be placed directly on the top surface of the first core member 34.

Instead of using two or more materials having different magnetic permeabilities, the first core member 34 can be made of a single material having an identical magnetic permeability. However, as shown in FIG. 5, one or more slits or grooves 74 can be disposed at an outer surface of the first core member 34.

Exemplary dimensions of each slit 74 include an opening width of approximately one (1) millimeter and a depth facing a central longitudinal axis of the first core member 34 of approximately ten (10) millimeters. In another embodiment, the slits 74 are also disposed at the outer surface of the second core member 38.

In this configuration, due to the slits 74, the formation of the magnetic flux is resisted more in the outer region 68 of the first core member 34 than in the inner region 70 of the first core member 34. Also, the magnetic flux in transmission around the inner region 70 of the first core member 34 is less resisted than around the outer region 68 of the first core member 34.

Thus, the magnetic force associated with the magnetic flux density is substantially equal near the top surface of the first core member 34 due to the existence of the slits 74. As a result, the magnetic force is substantially evenly applied to the magnetically-labeled cells 14 in the culture vessel 22. As such, the magnetic force applied substantially transversely to a plane (e.g., a layer) defined by the cell sheet 12 is also substantially evenly distributed.

Figure 6:
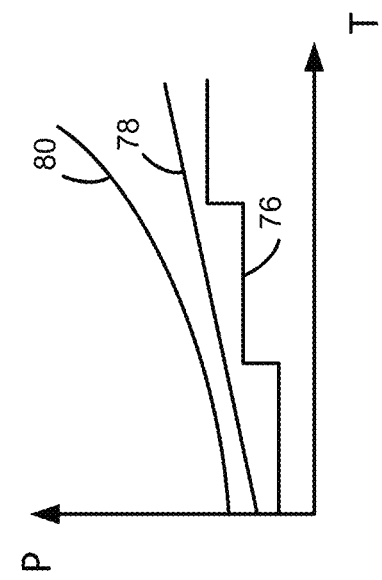
FIG. 6 is a graph illustrating characteristics of exemplary power control methods performed by the magnetic-field generator of FIG. 2.

Referring now to FIG. 6, exemplary power control methods performed by the power control system 44 (FIG. 2) are shown in accordance with embodiments of the present disclosure. In FIG. 6, a horizontal X-axis represents a time period T, and a vertical Y-axis represents a power level P of the first coil 46 and second coil 48 set by the power control system 44.

In one embodiment, as shown in a first segment 76, the controller 26 of the power control system 44 instructs the power source 50 or 52 to adjust or change (e.g., increase or decrease) the electric power supplied to the first coil 46 and the second coil 48 in a stepped manner. In another embodiment, as shown in a second segment 78, the controller 26 instructs the power source 50 or 52 to increase or decrease the electric power supplied to the first coil 46 and the second coil 48 as a linear function of time. In yet another embodiment, as shown in a third segment 80, the controller 26 instructs the power source 50 or 52 to increase or decrease the electric power in a non-linear fashion.

Referring now to FIG. 7, the magnetic-field generator 10 includes a cooling system 82 configured to cool the first table member 36 of the magnetic circuit assembly 24 in thermal communication with a cooling device 84 (e.g., a pump) using a coolant (e.g., water or air). To keep the magnetically-labeled cells 14 in the culture vessel 22 active and living during operation, a certain level of temperature (e.g., approximately 37° C.) is maintained.

For example, during operation, the controller 26 receives information about the current temperature of the first table member 36 from the temperature sensor 56 via the communication link 54. Then, the controller 26 instructs the cooling device 84 to deliver the coolant into a passageway 86 disposed in the first table member 36 based on the current temperature of the first table member 36.

Figure 9:
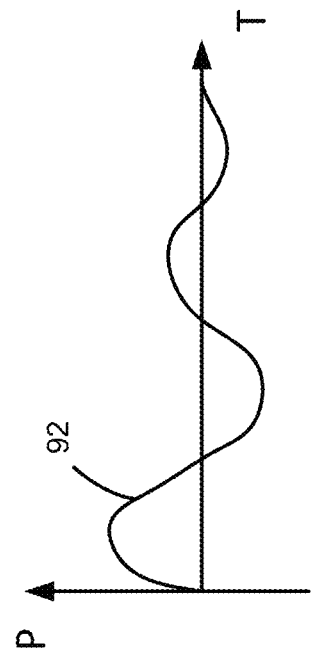
FIG. 9 is a graph illustrating characteristics of another exemplary power control method performed by the magnetic-field generator of FIG. 2.
Figure 8:
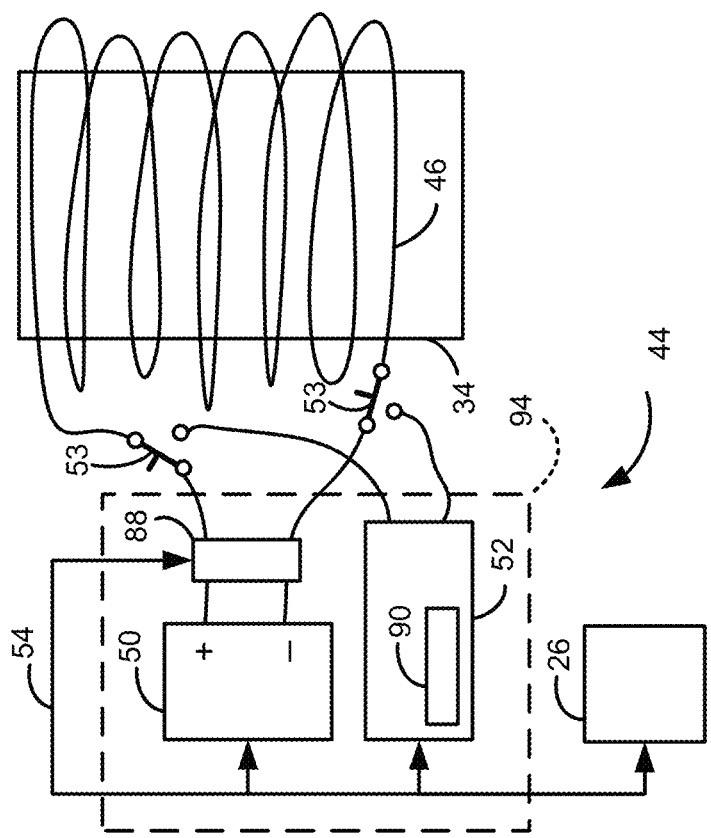
FIG. 8 illustrates a schematic diagram of a power control system used with the magnetic circuit assembly of FIG. 2.

Referring now to FIGS. 8 and 9, exemplary magnetic coercivity control methods performed by the power control system 44 (FIG. 2) are shown in accordance with embodiments of the present disclosure. After constructing the cell sheet 12 (FIG. 1), the controller 26 of the power control system 44 instructs the power source 50 or 52 to cease supplying the electric power to the first coil 46 and the second coil 48.

However, even if the electric power is no longer supplied to the first coil 46 and the second coil 48, the magnetic field still remains surrounding the first core member 34 and the second core member 38 for a certain time period. To avoid unwanted residual magnetism or flux caused by the remaining magnetic field, it is desirable to make the first core member 34 and the second core member 38 with a ferromagnetic material having low magnetic coercivity. In one embodiment, the low magnetic coercivity is defined as less than approximately one thousand ampere per meter (1,000 A/m).

In another embodiment, to negate the remaining magnetic field, a corresponding polarity of each of the first core member 34 and the second core member 38 is reversed. In the illustrated embodiment, a reverse current switch 88 configured to reverse a current polarity of the first core member 34 is electrically coupled between the first coil 46 and the DC power source 50, and also communicably coupled with the controller 26 via the communication link 54.

For example, the controller 26 of the power control system 44 instructs the reverse current switch 88 to reverse a flow of the electric current of the first coil 46 in an opposite direction to demagnetize the first core member 34. Although the reverse current switch 88 is shown separately in FIG. 8, the reverse current switch 88 can be integrated into the DC power source 50 as a single unit or any other components of the magnetic-field generator 10 to suit different applications.

In yet another embodiment, to negate the remaining magnetic field, an alternating current (AC) controller 90 is electrically coupled with the AC power source 52, and also communicably coupled with the controller 26 via the communication link 54. In the illustrated embodiment, the AC controller 90 is configured to control an amplitude or cycle period of the electric current supplied by the AC power source 52.

In FIG. 8, although the AC controller 90 is shown inside the AC power source 52, the AC controller 90 can be an independent unit or can be integrated with any other components of the magnetic-field generator 10 to suit different applications. In some embodiments, AC-to-AC or DC-to-AC converters or inverters can be used to suit different applications.

In FIG. 9, a segment 92 represents the AC current supplied to the first coil 46 by the AC power source 52. During operation, the AC controller 90 instructs the AC power source 52 to adjust or change the power level P of the AC current over a predetermined time period T. For example, the amplitude of a sinusoidal alternating voltage of the AC power source 52 is gradually diminished over the predetermined time period T. As such, the unwanted residual magnetism around the first core member 34 is promptly diminished using the AC controller 90.

Returning now to FIG. 8, although the reverse current switch 88 and the AC controller 90 are used to control the electric current supplied to the first coil 46, a similar configuration can be applied to the second coil 48 to suit different applications. Further, different power sources, such as the DC power source 50 and the AC power source 52, can be disposed in a single power manager 94 along with the reverse current switch 88 and the AC controller 90.

In one embodiment, the controller 26 is configured to control an overall operation of the power manager 94 via the communication link 54. Other suitable arrangements of the components 50, 52, 88, 90 of the magnetic-field generator 10 are also contemplated to suit the application. For example, the controller 26 instructs the power manager 94 to diminish the unwanted residual magnetism associated with the magnetic circuit assembly 24.

The present disclosure is more easily comprehended by reference to the specific embodiments, examples and drawings recited hereinabove which are representative of the present disclosure. It must be understood, however, that the same are provided for the purpose of illustration, and that the present disclosure may be practiced otherwise than as specifically illustrated without departing from its spirit and scope. As will be realized, the present disclosure is capable of various other embodiments and that its several components and related details are capable of various alterations, all without departing from the basic concept of the present disclosure. Accordingly, descriptions will be regarded as illustrative in nature and not as restrictive in any form whatsoever. Modifications and variations of the system, method, and apparatus described herein will be obvious to those skilled in the art. Such modifications and variations are intended to come within the scope of the appended claims.

What is claimed is:

1. A magnetic-field generator used in construction of a cell sheet, comprising:
a magnetic circuit assembly configured to generate a magnetic field for the construction of the cell sheet using magnetic force caused by the magnetic field; and
a power control system configured to generate and control electric power to magnetically charge the magnetic circuit assembly using the electric power,
wherein the magnetic circuit assembly includes at least one core member and at least one magnetic or ferromagnetic table member, and a common width of each of the at least one table member is greater than a common width of each of the at least one core member; and
wherein each of the at least one core member has an outer region and an inner region, and a magnetic permeability of the outer region is different from the magnetic permeability of the inner region.

2. The magnetic-field generator of claim 1, wherein the magnetic permeability of the outer region is lower than the magnetic permeability of the inner region.

3. The magnetic-field generator of claim 1, wherein each of the at least one core member has at least one slit disposed at an outer surface of the at least one core member.

4. The magnetic-field generator of claim 1, wherein the power control system is configured to adjust a power level of the electric power.

5. The magnetic-field generator of claim 1, further comprising a cooling system configured to cool the magnetic circuit assembly.

6. The magnetic-field generator of claim 1, further comprising an extraction device configured to extract a culture supernatant associated with the cell sheet.

7. The magnetic-field generator of claim 1, wherein the magnetic circuit assembly comprises a ferromagnetic material having a low magnetic coercivity of less than one thousand amperes per meter.

8. The magnetic-field generator of claim 1, further comprising a power manager configured to diminish unwanted residual magnetism associated with the magnetic circuit assembly.

9. The magnetic-field generator of claim 1, wherein the magnetic force is substantially transverse to a plane defined by the cell sheet, and the magnetic force being substantially transverse penetrates the cell sheet and a direction of the penetrating magnetic force is approximately ninety degrees with respect to the plane defined by the cell sheet.

10. The magnetic-field generator of claim 1, wherein the at least one table member includes a first table member and a second table member.

11. The magnetic-field generator of claim 10, wherein the first table member and the second table member are disposed to be separated from each other such that an air gap is created between the first table member and the second table member.

12. The magnetic-field generator of claim 11, wherein the air gap between the first table member and the second table member is configured for facilitating insertion of a culture vessel having the cell sheet.

13. The magnetic-field generator of claim 1, further comprising a passageway configured for placing each of the at least one core member and each of the at least one table member in fluid communication with one another, and configured to facilitate extraction of at least a portion of the cell sheet.

14. A magnetic-field generator used in construction of a cell sheet, comprising:
a magnetic circuit assembly configured to generate a magnetic field for the construction of the cell sheet using magnetic force caused by the magnetic field; and
a power control system configured to generate and control electric power to magnetically charge the magnetic circuit assembly using the electric power,
wherein the magnetic circuit assembly includes at least one core member and at least one table member, and a common width of each of the at least one table member is greater than a common width of each of the at least one core member; and wherein each of the at least one core member has at least one slit disposed at an outer surface of the at least one core member.

15. A magnetic-field generator used in construction of a cell sheet, comprising:
   a magnetic circuit assembly configured to generate a magnetic field for the construction of the cell sheet using magnetic force caused by the magnetic field; and
   a power control system configured to generate and control electric power to magnetically charge the magnetic circuit assembly using the electric power,
   wherein the magnetic circuit assembly includes at least one core member and at least one table member, and a common width of each of the at least one table member is greater than a common width of each of the at least one core member;
   wherein each of the at least one table member includes a first table member and a second table member; and
   wherein each of the first table member and the second table member is disposed to be separated from each other such that an air gap is created between the first table member and the second table member.

16. A magnetic-field generator used in construction of a cell sheet, comprising:
   a magnetic circuit assembly configured to generate a magnetic field for the construction of the cell sheet using magnetic force caused by the magnetic field; and
   a power control system configured to generate and control electric power to magnetically charge the magnetic circuit assembly using the electric power,
   wherein the magnetic circuit assembly includes at least one core member and at least one table member, and a common width of each of the at least one table member is greater than a common width of each of the at least one core member; and
   a passageway configured for placing each of the at least one core member and each of the at least one table member in fluid communication with one another, and configured to facilitate extraction of at least a portion of the cell sheet.

17. The magnetic-field generator of claim 16, wherein the air gap between the first table member and the second table member is configured for facilitating insertion of a culture vessel having the cell sheet.

* * * * *